United States Patent [19]

Morrissey

[11] Patent Number: 4,468,466

[45] Date of Patent: Aug. 28, 1984

[54] SILVER STAINS FOR PROTEIN IN GELS—A MODIFIED PROCEDURE

[75] Inventor: James H. Morrissey, Oxford, England

[73] Assignee: The United States of America as represented by the Department of Health and Human Services, Washington, D.C.

[21] Appl. No.: 349,313

[22] Filed: Feb. 16, 1982

[51] Int. Cl.³ ............................................. G01N 33/68
[52] U.S. Cl. ........................................ 436/86; 436/169
[58] Field of Search ................... 436/86, 87, 88, 169, 436/515

[56] References Cited

U.S. PATENT DOCUMENTS 4,405,720  9/1983  Merril ........................... 436/169 X
4,416,998  11/1983  Adams et al. ........................ 436/86

OTHER PUBLICATIONS

Kerenyi, et al., "A Highly Sensitive Method for Demonstrating Proteins in Electrophoretic, Immuno-electrophoretic and Immuno-diffusion Preparations", *Clin. Chim. Acta*, 38, 465–467 (1972).

Kerenyi, et al., "Uber Problems der Quantitiven Auswertung der mit Physikalischer Entwicklung Versilberten Agarelektrophoretogramme", *Clin. Chim. Acta*, 47, 425–436 (1973).

Veerheecke, "Agargel Electrophoresis of Unconcentrated Cerebrospinal Fluid", *J. Neurol.*, 209, 59–63 (1975).

Karcher, et al., "Cerebrospinal Fluid Proteins Electrophoresis without Prior Concentration", *Acta Neurol. Belg.*, 79, 335–337 (1979).

Switzer, et al., "A Highly Sensitive Silver Stain for Detecting Proteins and Peptides in Polyacrylamide Gels", *Anal. Biochem*, z8, 231–237 (1979).

Merril, et al., "Trace Polypeptides in Cellular Extracts and Human Body Fluids Detected by Two-Dimensional Electrophoresis and a Highly Sensitive Silver Stain", *Proc. Natl. Acad. Sci. U.S.A.*, 76, 4335–4339 (1979).

Oakley, et al., "A Simplified Ultrasensitive Silver Stain for Detecting Proteins in Polyacrylamide Gels", *Anal. Biochem.* 105, 361–363 (1980).

Merril, et al., in Anal. Biochem., 110:201–207 (1981).

Merril, et al., in Science, 211:1437–1438 (1981).

Sun, et al., in Cell 9:511–521 (1976).

*Primary Examiner*—Arnold Turk
*Assistant Examiner*—Robert J. Hill, Jr.
*Attorney, Agent, or Firm*—Holman & Stern

[57] ABSTRACT

In a silver stain method for protein in gels utilizing treatment with a reducing agent followed by treatment with a silver salt and actuating irradiation, the improvement comprising the use of a reducing agent consisting essentially of dithiothreitol in an amount effective to stain the protein but keep background staining to a minimum.

8 Claims, No Drawings

SILVER STAINS FOR PROTEIN IN GELS—A MODIFIED PROCEDURE

BACKGROUND OF THE INVENTION

1. Field of the Invention

This invention relates to improved ultra-sensitive metallic silver stains for proteins/polypeptides, especially when fixed in synthetic gels, particularly polyacrylamide gels.

2. Description of the Prior Art

Detection and characterization of polypeptides is of fundamental importance to many areas of biology and clinical medicine. In some endeavors, such as genetic screening for mutational events, monitoring for pathophysiologic changes in disease states, and the diagnosis of genetic diseases, the efficiency of the search is directly proportional to the number of polypeptides that can be detected and characterized in cellular extracts of body fluids. Additionally polypeptides, hormones, etc., that are present in trace amounts are often of great importance for various medical reasons.

Electrophoresis (defined generally as the movement of charged particles in solution under the influence of an electrical field), is a primary laboratory detection and characterization technique, especially useful for polypeptides and other macromolecules, such as nucleic acids. It is also useful in separating small particles such as viruses, cells, sub-cellular organelles and organic molecules such as steroids and amino acids.

Continuing developments in two-dimensional gel electrophoresis have provided the capability of resolving thousands of polypeptides from complex biological mixtures. However, the inability to detect polypeptides present in low concentration has limited the application of this technology, particularly in clinical screening for pathological states, endocrinology, mammalian metabolism, developmental biology, and immunology.

Because the improved gel electrophoretic techniques greatly increase polypeptide resolution, visual detection methods employing conventional polypeptide dyes are no longer adequate.

The most commonly used conventional polypeptide stain is Coomassie Blue, which may be considered as a prototype. Dyes of this type are mainly dependent upon the electrostatic attraction between dye and polypeptide, stabilized by van der Wall's forces. In fact, Coomassie Blue and a variety of other dyes exhibit particular affinities for polypeptides of specific charge. Coomassie Blue, an acidic dye, stains basic polypeptides most intensely, while crystal violet is the most effective stain for acidic polypeptides. Other dyes for which quantitative aspects of staining have been investigated include Amido Black, Fast Green, and $Fe^{2+}$-bathophen-nanthroline sulfonate. In contrast, the Remazol Brilliant Blue R method depends on a covalent bond between dye and polypeptide. With Coomassie Blue, linearity has been found, by staining for 30 minutes in 1.5 mm diameter gels, in the polypeptide concentration range of 0.05–2 $\mu$g using the parameter of relative spot area. Staining for 60 rather than 30 minutes may result in an increase in the slope of the area/concentration relationship and nonlinearity due to saturation above 1 $\mu$g. Fluorescamine can react with terminal and $\epsilon$-amino groups of polypeptides in gels to achieve a sensitivity at least equal to that of Coomassie Blue, with linearity from 1 to 7 $\mu$g "per spot". MDPF (2-methoxy-2-4-diphenyl-3(2H)-furanone) may be used to label polypeptides fluorescently prior to electrophoresis, with linearity from 10 ng to 10 $\mu$g of protein. However fluorescent staining of polypeptides prior to electrophoresis may alter their electrophoretic patterns.

An assortment of other techniques which do not require modification of proteins/polypeptides prior to electrophoresis also exist. These include densitometric scanning for absorbance at 280 nm, binding of radiolabelled or fluorescent ligands such as concanavalin A to glycoproteins, binding of antisera to polypeptides at the gel surface, and staining of specific polypeptide moieties including carbohydrate sidechains with PAS, sulfhydryl groups with 5,5'-dithiobis (2-nitrobenzoic acid), copper polypeptides with cyanide-tetrazolium, cadmium polypeptides with dipyridyl-ferrous iodide and $Ca^{2+}$-polypeptides with $^{45}Ca$ autoradiography.

Radioactive detection techniques offer a higher degree of sensitivity than the stains but are often impractical to use. In vivo radiolabelling may alter cellular metabolism and it may be impossible to label certain human polypeptides. In vitro radiolabelling has the disadvantage that it might alter the electrophoretic mobility of polypeptides. Furthermore, radioactive reagents sometimes prove too expensive and long exposure to detect trace polypeptide may result in the problem of "autoradiographic spreading".

The above staining methods, moreover, are difficult to perform, hazardous, time consuming, and unless the polypeptides are heavily labeled, lack the sensitivity to detect proteins present in low or trace concentrations. A problem arises, for example, with body fluids, such as cerebrospinal and amniotic fluids, which are often difficult to obtain in quantity and frequently contain certain abundant proteins which cause distortion of electrophoretic patterns when sufficient sample is analyzed to observe specific trace polypeptides.

Recently, highly sensitive silver strain methods for polypeptides in polyacrylamide gels have been developed. These methods have the disadvantages of being too wasteful of silver and/or being too complicated, and in most instances are less sensitive or reproducible than the improved method of this invention, although more sensitive than non-silver stains.

[Ref. 1] Kerényi and Gallyas, in "A Highly Sensitive Method for Demonstrating Proteins in Electrophoretic, Immuno-electrophoretic and Immuno-diffusion Preparations", *Clin. Chim. Acta*, 38, 465–467 (1972) disclose a silver stain for proteins in agar gel in which the gel is immersed in potassium ferrocyanide, and then in a two solution developer containing sodium carbonate and water in the first solution and ammonium nitrate, silver nitrate, tungsto-silicic acid, and formaldehyde in the second solution. The possibility of using polyacrylamide gel is mentioned.

[Ref. 2] Keréyni and Gallyas, in "Über Probleme der Quantitiven Auswertung der mit Physikalischer Entwicklung Versilberten Agarelektrophoretogramme", *Clin. Chim. Acta*, 47, 425–436 (1973) continued the study of the silver stain disclosed in 1972, above. Artifacts developed during the staining, whose avoidance is discussed.

[Ref. 3] Veerheecke, in "Agargel Electrophoresis of Unconcentrated Cerebrospinal Fluid", *J. Neurol*, 209, 59–63 (1975) discloses silver staining in agar gel utilizing two solutions after immersion of the protein-containing gel in potassium ferrocyanide. The first solution contains sodium carbonate in water, the second solution contains ammonium nitrate, water, formaldehyde, and tungsto-silicic acid as well as silver nitrate. The results reported are mixed, although generally favorable. Mention is made that the method of Kerényi and Gallyas (1972), supra, of which this was a replication, did not appear to have found widespread acceptance, possibly because discrete bands in the gamma region of the electropherogram could not be detected and because numerous artifacts were experienced. Veerheecke himself experienced difficulties with bands in several regions.

[Ref. 4] Karcher, Lowenthal and Van Soom, in "Cerebrospinal Fluid Proteins Electrophoresis without Prior Concentration", *Acta neurol. Belg.*, 79, 335–337 (1979), disclose silver staining utilizing two solutions after immersion of the protein-containing gel in potassium ferrocyanide. The first solution contains sodium carbonate, the second solution contains ammonium nitrate, water, formaldehyde, and tungsto-silicic acid as well as silver nitrate. The disclosure concludes that the stain is comparable to that obtained for conventional electrophoresis staining with amido-black, working with concentrated cerebrospinal fluid.

[Ref. 5] Switzer, Merril and Shifrin, in "A Highly Sensitive Silver Strain for Detecting Proteins and Peptides in Polyacrylamide Gels", *Anal. Biochem*, 98, 231–237 (1979), discloses a silver stain in which the proteins are fixed by soaking of the gel in various methanol/acetic acid mixtures for at least 2.5 hours, soaking the gel in a paraformaldehyde solution for 0.5 hours, placing the gel in a cupric nitrate/silver nitrate solution for at least 0.5 hours, placing the gel in a diammine solution (a mixture of silver nitrate, NaOH, NH$_4$OH, and ethanol) for 10 min., and twice reducing the gel strain with formaldehyde and citric acid. The stain was found to be 100 times more sensitive than Coomassie Blue and comparable to autoradiography.

[Ref. 6] Merril, Switzer, and Van Keuren, in "Trace Polypeptides in Cellular Extracts and Human Body Fluids Detected by Two-Dimensional Electrophoresis and a Highly Sensitive Silver Stain", *Proc. Natl. Acad. Sci. U.S.A.*, 76, 4335–4339 (1979), utilized the stain disclosed by Reference 5, above. Some potential clinical applications were demonstrated as well as that the stain was more sensitive than Coomassie Blue, and less expensive and more rapid than autoradiography.

[Ref. 7] Oakley, Kirsch and Morris, in "A Simplified Ultrasensitive Silver Stain for Detecting Proteins in Polyacrylamide Gels", *Anal. Biochem*. 105, 361–363 (1980), discloses an adaptation of the silver stain first disclosed in Reference 5, above. The disclosed process utilizes (1) soaking the gel in glutaraldehyde for 30 minutes, (2) rinsing and soaking the gel in water for at least 2 hours, (3) adding ammoniacal silver solution (a mixture of NH$_4$OH, NAOH, and AgNO$_3$), (4) transferring the gel to a mixture of citric acid and formaldehyde, and (6) washing in water for at least 1 hour. The stated advantages are simplification of the original procedure, elimination of the cupric-silver nitrate step, and reduction of the amount of silver required.

[Ref. 8] Nerril, Donau and Goldman, in *Anal. Biochem.*, 110:201–207 (1981) and [Ref. 9] Merril, Goldman, Sedman and Ebert, in Science, 211:1437–1438 (1981), both disclose silver stains particularly useful for detecting proteins in trace quantities and for staining two-dimensional electrophoresced gels. However, there appears to be considerable variation in sensitivity from gel to gel and some proteins which stain well with Coomassie Blue do not stain with these silver stains. Further, these stain methods require a source of activating irradiation such as high intensity light.

[Ref. 10] Sun and Green, in Cell 9:511–521 (1976) have found that treating tissues with 2-mercaptoethanol (HSCH$_2$CH$_2$OH) immediately prior to silver impregnation in histological stains gave much more reproducible results. Mercaptoethanol has known use as a water-soluble reducing agent and as a non-nitrogenous sulfhydryl reagent in the investigation of proteins [see the "Condensed Chemical Dictionary" 6th ed., Reinhold Pub., N.Y., 1961].

SUMMARY OF THE INVENTION

It has been found that the use of dithiothreitol to treat gels prior to silver nitrate treatment, in an otherwise conventional ultrasensitive silver stain, results in staining patterns that are more consistently reproducible and desireably more closely resemble those obtained with Coomassie Blue. For example, in using the sensitive silver stain procedure of Reference 9, dithiothreitol treatment replaces the dichromate step. An important and completely unexpected further result of the use of dithiothreitol, is that the need for activating light irradiation is generally eliminated.

DESCRIPTION OF THE PREFERRED EMBODIMENTS

Dithiothreitol [D,L-theo-1,4-dimercapto-2,3-butanediol; Cleland's reagent; theo-2,3-dihydroxy1,4-dithiolbutane] is mentioned in *The Merck Index*, 9th ed., Merck & Co., Inc., Rahway, N.J., U.S.A. (1976) as being used as a protective agent for SH groups, and is mentioned in *Aldrichimica Acta*, 4:33 (1971) as a thiol reagent. This compound is listed in the 1981–1982 *Aldrich Catalog Handbook of Fine Chemicals*, Aldrich Chemical Co., Milwaukee, Wis., U.S.A. (1980).

As employed in this invention, dithiothreitol acts as a reducing agent to effect "photoreversal" and avoid silver staining of non-proteins. Dithiothreitol has been found to be an unexpected and superior replacement for known silver stain oxidizing agents such as potassium ferricyanide and dichromates. Functionally related reducing agents such as 2-mercaptoethanol (see Reference 10) and chloral hydrate have similar effects. However, when these functionally related reducing agents were tried, it was found that only the dithiothreitol of this invention was effective at very low concentrations, and only these concentrations were sufficiently low to keep background staining to a minimum.

It is not known why the use of a known reducing agent in place of a known oxidizing agent should yield an improved result, contrary to what might have been expected. Another unexpected result, is that the light irradiation required in prior art silver stains discussed above, may be completely eliminated. This greatly reduces the equipment needed to perform the silver stains, although there may be some instances in which light irradiation is useful in the improved silver stains of this invention.

The improved silver stains according to this invention are performed sequentially as follows:

Step 1. Prefix the gel in 50% methanol/10% acetic acid for 30 minutes, followed by 5% methanol/7% acetic acid for 30 minutes.

Step 2. Fix the gel for 30 minutes in 10% glutaraldehyde.

Step 3. Rinse the gel in distilled water. It is most convenient to soak the gel in a large volume of water overnight, followed by a fresh water rinse the next day for 30 minutes. Alternatively, the gel may be washed in running deionized water, or several changes of water, for 2 hours.

Step 4. Soak the gel in a reducing agent consisting essentially of 5.0 μg/ml dithiothreitol for 30 minutes. This step, which replaces treatment with oxidizing agents such as the dichromates disclosed in the prior art, is the critical improvement of this invention over the prior art.

Step 5. Pour off the dithiothreitol solution, and without rinsing, add 0.1% silver nitrate and soak for 30 minutes. This step is another improved aspect of this invention, in that no actuating irradiation, such as exposure to intense light, is necessary or preferred.

Step 6. Rinse the gel once rapidly with distilled water and then twice rapidly with developer. Soak in developer (50 μl of 37% formaldehyde in 100 ml 3% sodium carbonate) until the desired level of staining is attained. Staining is stopped by adding 5 ml of 2.3 M citric acid directly to the developer and agitating for 10 minutes. This solution is then discarded and the gel is washed several times in distilled water over a 30 minute period. For storage, it is preferred to soak the gel for 10 minutes in 0.03% sodium carbonate (to prevent bleaching), and then to seal the gel in plastic bags, cellophane, or the like.

Gentle but thorough agitation is highly recommended throughout the above procedure. The times in the above procedures are approximate and times of 10 minutes may vary by ±5 minutes, times of 30 minutes±10 minutes and times of 2 hours±30 minutes, unless otherwise indicated. The quantities and identities of reagents used in the above procedure are not critical and may be varied as disclosed in the art, with the notable exception of the dithiothreitol of Step 5. The use of the dithiothreitol constitutes one of the two critical improvements of this invention. As disclosed herein, substitution for the dithiothreitol by functionally related compounds such as 2-mercaptoethanol or chloral hydrate does not yield satisfactory status, because only dithiothreitol is effective at sufficiently low concentrations as to keep background staining to a minimum. The concentration of the dithiothreitol as used in Step 4, therefore also constitutes a critical aspect of this invention. A dithiothreitol concentration of from about 2.0 to about 10.0 μg/ml is permissible, with 4.0 to 6.0 μg/ml being preferred and about 5.0 μg/ml being optimum. The soaking with the dithiothreitol solution may be for about 15 to about 45 minutes, with 25 to 35 minutes being preferred and about 30 minutes being optimum.

Preferably, the gels are fixed and stained in polyethylene containers which have been cleaned with nitric acid. The same container may be used throughout the procedure. Typically, for gels of 1 mm×9 mm×13 cm dimensions, all volumes are 100 ml, except for the 10% glutaraldehyde which is 50 ml. These volumes should be adjusted accordingly if different size gels are used. Particular attention should be paid to the volumes of the carbonate and citric acid solutions, which must be balanced to bring pH to about 7. If the pH remains too high, the reaction will not stop, and if the pH falls too low, the gel will bleach.

All gel compositions suitable for use in electrophoresis may be used in this invention. Typical gels are polyacrylamide, agarose, and cellulose acetate. Polyacrylamide is preferred, and it may be assumed that all references to "gel" denote a 10% polyacrylamide gel, unless indicated otherwise.

As with other silver stain methods, the gels utilized are fragile. They should be handled only with rinsed plastic gloves to avoid stained fingerprints on the gel. Another source of contamination that can cause spurious staining is dust in the gel solutions. It is advisable that all solutions be filtered through microporous filters prior to use.

EXAMPLES AND DISCUSSION

In the course of replicating published silver stains for gels, disclosed in the discussed references, it was found that certain proteins fail to show any staining, while the staining of other proteins varies considerable from gel to gel. For example, *D. discoideum* spore coat protein sp 96 strains with Coomassie Blue but not with the silver staining methods of References 7 or 8. This protein failed to stain with either silver stain in at least twenty attempts. When molecular weight marker proteins are stained, both silver stains showed reduced sensitivity to insulin B chain, and in this gel the method of Reference 8 showed little sensitivity to cytochrome C. Occasionally, the method Reference 7 has been found to give a staining pattern with insulin B chain and bovine serum albumin which consists of a ring staining surrounding an unstained band. In some cases with this procedure conalbumin exhibits negative staining, in that an unstained area considerably lighter than the background is found in place of a stained band. The procedure of Reference 8 could not be replicated in its staining of whole cell proteins. A few bands were extremely dark, while the bulk of the cellular proteins stain considerably less well than with Coomassie Blue.

Variable and unreliable staining reactions have been observed with histological silver stains; however, Reference 10 discloses that treating tissues with 2-mercaptoethanol immediately prior to silver impregnation gives much more reproducible results, and is discussed previously.

Examples of actual procedures according to this invention that were utilized in preparing silver stains are as follows:
1. 50% methanol, 10% acetic acid—30 min.
2. 5% methanol, 7% acetic acid—30 min.
3. 10% glutaraldehyde—30 min.
4. deionized water, several changes—2 hrs. to overnight.
5. 5 μg/ml dithiothreitol—30 min.
6. 0.1% silver nitrate—30 min.
7. rinse rapidly once with distilled water, then twice rapidly with a small amount of developer.
8. developer—until staining reaches desired intensity.
9. add 5 ml 2.3 M citric acid directly to the developer (solution will fizz)—10 min.
10. several rinses in distilled water over a 30 min. period.
11. 0.03% sodium carbonate (to prevent bleaching)—10 min.

The developer was 50 μl 37% formaldehyde in 100 ml 3% sodium carbonate.

Using the above stain, it was found that sp 96 (see above) stained well, as did all of the molecular weight marker proteins. The total cellular protein pattern resembled that of Coomassie Blue. The stain was found to be highly reproducible.

Among the advantages of the improved silver stains of this invention, are: (1) they use significantly less silver than the prior art stains; (2) they do not require special high-intensity light sources; (3) unlike ammoniacal silver stains, they do not employ unstable or potentially explosive solutions; and (4) there is virtually no surface deposition of silver, substantially reducing background staining.

The invention method is at least as sensitive as the previous published methods. Sensitivities of selected proteins are: 0.042 ng/mm$^2$ for bovine serum albumin, 0.083 ng/mm$^2$ for ovalbumin, and 0.17 ng/mm$^2$ for cytochrome C. These values compare favorably to those of References 7 and 8.

I claim:

1. In a silver stain method for protein in gels utilizing treatment with a reducing agent followed by treatment with a silver salt and actuating irradiation, the improvement comprising the use of a reducing agent consisting essentially of dithiothreitol in an amount effective to stain the protein but keep background staining to a minimum.

2. The improvement of claim 1 wherein the dithiothreitol is used in a concentration of from about 2.0 to about 10.0 μg/ml and the protein in gel being treated is soaked therein for a time of about 15 to about 45 minutes.

3. The improvement of claim 2 wherein the concentration is from 4.0 to 6.0 μg/ml and the time is 25 to 35 minutes.

4. The improvement of claim 3 wherein the concentration is about 5.0 μg/ml and the time is about 30 minutes.

5. In a silver stain method for protein in gels utilizing treatment with a reducing agent followed by treatment with a silver salt, the improvement comprising the use of a reducing agent consisting essentially of dithiothreitol in an amount effective to stain the protein but keep background staining to a minimum.

6. The improvement of claim 5 wherein the dithiothreitol is used in a concentration of from about 2.0 to about 10.0 μg/ml and the protein in gel being treated is soaked therein for a time of about 15 to about 45 minutes.

7. The improvement of claim 6 wherein the concentration is from 4.0 to 6.0 μg/ml and the time is 25 to 35 minutes.

8. The improvement of claim 7 wherein the concentration is about 5.0 μg/ml and the time is about 30 minutes.

* * * * *